United States Patent
Yamasaki et al.

(10) Patent No.: US 10,363,016 B2
(45) Date of Patent: Jul. 30, 2019

(54) PIEZOELECTRIC ELEMENT, ULTRASONIC PROBE, ULTRASONIC MEASUREMENT DEVICE, AND MANUFACTURING METHOD OF PIEZOELECTRIC ELEMENT

(71) Applicant: SEIKO EPSON CORPORATION, Tokyo (JP)

(72) Inventors: Sayaka Yamasaki, Suwa (JP); Hiroaki Tamura, Shimosuwa-machi (JP)

(73) Assignee: SEIKO EPSON CORPORATION, Tokyo (JP)

( * ) Notice: Subject to any disclaimer, the term of this patent is extended or adjusted under 35 U.S.C. 154(b) by 296 days.

(21) Appl. No.: 15/360,822

(22) Filed: Nov. 23, 2016

(65) Prior Publication Data

US 2017/0143308 A1 May 25, 2017

(30) Foreign Application Priority Data

Nov. 25, 2015 (JP) .................. 2015-229831

(51) Int. Cl.
| | |
|---|---|
| *A61B 8/00* | (2006.01) |
| *A61B 8/14* | (2006.01) |
| *H01L 41/09* | (2006.01) |
| *H01L 41/113* | (2006.01) |
| *H01L 41/312* | (2013.01) |
| *H01L 41/338* | (2013.01) |
| *A61B 8/08* | (2006.01) |
| *B06B 1/06* | (2006.01) |
| *H01L 41/08* | (2006.01) |
| *H01L 41/31* | (2013.01) |

(52) U.S. Cl.
CPC .......... *A61B 8/4494* (2013.01); *A61B 8/0891* (2013.01); *A61B 8/14* (2013.01); *A61B 8/4427* (2013.01); *B06B 1/0629* (2013.01); *H01L 41/081* (2013.01); *H01L 41/09* (2013.01); *H01L 41/094* (2013.01); *H01L 41/0933* (2013.01); *H01L 41/113* (2013.01); *H01L 41/31* (2013.01); *H01L 41/312* (2013.01); *H01L 41/338* (2013.01); *A61B 8/4444* (2013.01)

(58) Field of Classification Search
CPC ....... A61B 8/4494; A61B 8/0891; A61B 8/14; A61B 8/4444; H01L 41/31; H01L 41/312; H01L 41/081
USPC .......................................... 310/334
See application file for complete search history.

(56) References Cited

U.S. PATENT DOCUMENTS

| | | | | |
|---|---|---|---|---|
| 6,198,208 B1 * | 3/2001 | Yano | ............... | H01L 41/1876 310/358 |
| 7,005,947 B2 * | 2/2006 | Iwashita | ............ | H03H 9/02574 310/313 A |

(Continued)

FOREIGN PATENT DOCUMENTS

| | | |
|---|---|---|
| JP | 60-206315 A | 10/1985 |
| JP | 2008-173177 A | 7/2008 |

*Primary Examiner* — Bryan P Gordon
(74) *Attorney, Agent, or Firm* — Maschoff Brennan

(57) ABSTRACT

A piezoelectric element, in which a piezoelectric body, and a vibrating plate having [111]-oriented single crystal silicon as a vibrating material are laminated is provided. In addition, a manufacturing method of a piezoelectric element including: cutting out a vibrating material to be used in the vibrating plate from a [111]-oriented single crystal silicon wafer; and laminating a piezoelectric body and the vibrating plate is provided.

7 Claims, 11 Drawing Sheets

(56) References Cited

U.S. PATENT DOCUMENTS

| | | | | |
|---|---|---|---|---|
| 7,851,977 B2* | 12/2010 | Ruile | ............... | H03H 9/0222 |
| | | | | 310/313 B |
| 2012/0319535 A1* | 12/2012 | Dausch | ............. | B06B 1/0622 |
| | | | | 310/365 |
| 2013/0056671 A1* | 3/2013 | Kubota | ............. | C04B 35/475 |
| | | | | 252/62.9 PZ |
| 2013/0193809 A1* | 8/2013 | Araki | ................ | H03H 3/02 |
| | | | | 310/365 |
| 2014/0062261 A1* | 3/2014 | Yamamoto | ......... | B06B 1/0622 |
| | | | | 310/334 |
| 2014/0292941 A1* | 10/2014 | Kobayashi | ........ | B06B 1/0629 |
| | | | | 347/68 |

* cited by examiner

[ SEC D-D ]

PIEZOELECTRIC ELEMENT, ULTRASONIC PROBE, ULTRASONIC MEASUREMENT DEVICE, AND MANUFACTURING METHOD OF PIEZOELECTRIC ELEMENT

BACKGROUND

1. Technical Field

The present invention relates to a piezoelectric element and the like.

2. Related Art

Biological information is measured by using an ultrasonic probe and an ultrasonic measurement device using a piezoelectric element as a transducer for ultrasonic transmitting and receiving, and vascular functions are evaluated or vascular diseases are determined. For example, JP-A-2008-173177, for example, discloses an ultrasonic probe and an ultrasonic measurement device which automatically detect vascular walls by using reflected wave signal intensity from biological tissues obtained by processing amplitude information of received ultrasonic waves and a moving velocity of biological tissues obtained by processing phase information of received ultrasonic waves.

A piezoelectric element used in the ultrasonic probe and the ultrasonic measurement device is prepared by laminating a piezoelectric body on a vibrating plate on a thin film, as disclosed in JP-A-60-206315, for example.

It was found that a single crystal silicon wafer used in the manufacturing of a general piezoelectric element has anisotropy in a Young's modulus or a Poisson's ratio, in accordance with plane orientation. However, in a manufacturing method of a piezoelectric element of the related art, a plurality of elements were simply spread on a single crystal silicon wafer, without particularly considering for anisotropy, patterned, and cut out to prepare a piezoelectric element. That is, even piezoelectric elements prepared by cutting out the same silicon wafer, vibrating properties of each piezoelectric element were different from each other and variations in properties of the piezoelectric elements occurred.

SUMMARY

An advantage of some aspects of the invention is to provide a piezoelectric element in which variations in properties due to anisotropy of a silicon wafer are prevented.

A first aspect of the invention is directed to a piezoelectric element in which a piezoelectric body, and a vibrating plate having [111]-oriented single crystal silicon as a vibrating material are laminated.

A Young's modulus and a Poisson's ratio of the [111]-oriented single crystal silicon wafer have no anisotropy due to a deviation angle, and a Young's modulus and a Poisson's ratio have isotropy. Accordingly, according to the first aspect of the invention, when the vibrating plate is prepared by using the [111]-oriented single crystal silicon wafer as a vibrating material, it is possible to significantly reduce a variation in properties due to anisotropy of the silicon wafer, compared to that in the related art, regardless of the position of the silicon wafer where the piezoelectric element to be prepared is patterned.

A second aspect of the invention is directed to an ultrasonic probe including: the piezoelectric element of the first aspect of the invention for transmitting ultrasonic waves.

A third aspect of the invention is directed to an ultrasonic probe including: the piezoelectric element of the first aspect of the invention for receiving ultrasonic waves.

A fourth aspect of the invention is directed to an ultrasonic probe including: the piezoelectric element of the first aspect of the invention for transmitting and receiving ultrasonic waves.

According to any one of second to fourth aspects of the invention, it is possible to realize an ultrasonic probe in which variations in properties of the piezoelectric element due to anisotropy of a silicon wafer are prevented.

A fifth aspect of the invention is directed to an ultrasonic measurement device including: the ultrasonic probe according to any one of the second to fourth aspects of the invention.

According to the fifth aspect of the invention, it is possible to realize an ultrasonic measurement device in which variations in properties of the piezoelectric element due to anisotropy of elasticity of a silicon wafer are prevented.

A sixth aspect of the invention is directed to a manufacturing method of a piezoelectric element including: cutting out a vibrating material to be used in a vibrating plate from a [111]-oriented single crystal silicon wafer; and laminating a piezoelectric body and the vibrating plate.

According to the sixth aspect of the invention, it is possible to manufacture a piezoelectric element having the same operation effects as those in the first aspect of the invention.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

Figure 1:
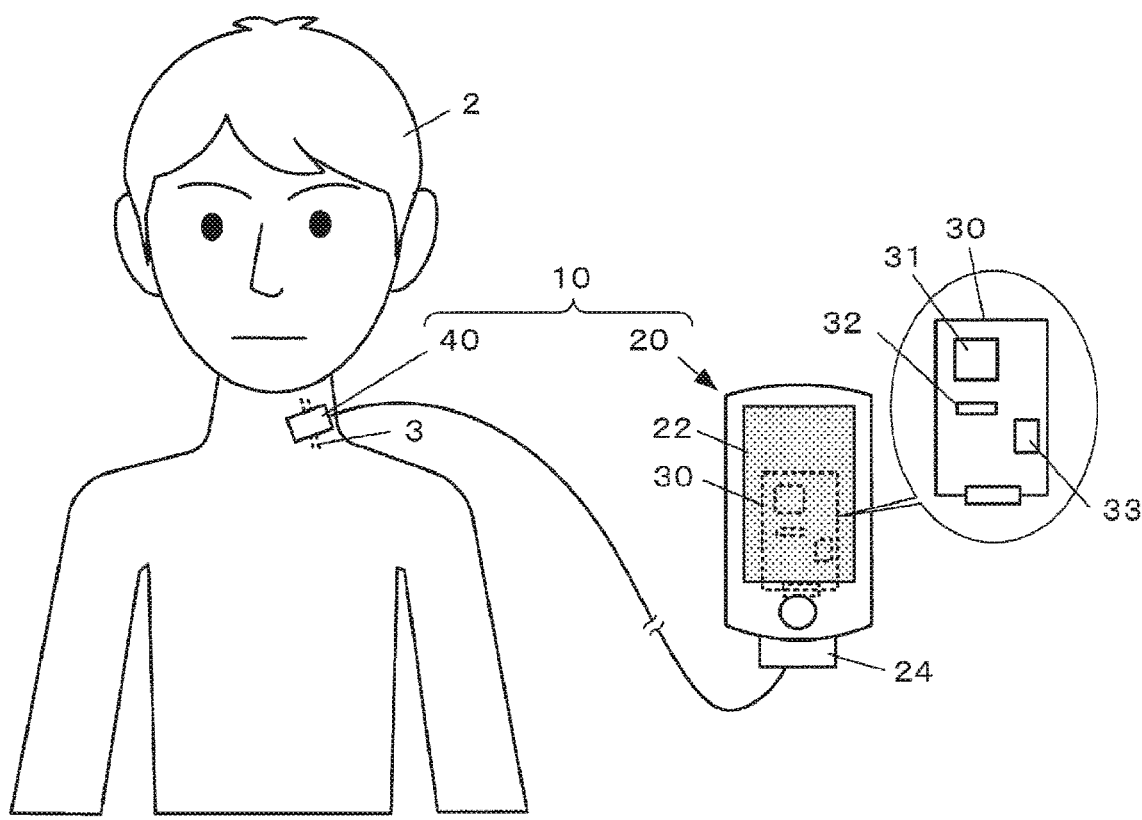
FIG. 1 is a view showing a system configuration example of an ultrasonic measurement device of a first embodiment.

FIG. 1 is a view showing a system configuration example of an ultrasonic measurement device 10 of an embodiment.

The ultrasonic measurement device 10 is a device which measures biological information of a subject 2 by transmitting ultrasonic waves to the subject 2 and measuring reflected waves. In the embodiment, vascular function information such as intima media thickness (IMT) of the carotid 3 is measured as one of the biological information items. In addition to the IMT, other vascular function information or biological information may be measured by estimating a blood vessel diameter or blood pressure from a blood vessel diameter or calculating a pulse from a change of a blood vessel diameter. A measurement target is not limited to a human.

The ultrasonic measurement device 10 includes a measurement control device 20 and an attaching-type ultrasonic probe 40.

The measurement control device 20 is a portable computer and includes a touch panel 22 which serves as both a unit for displaying an image of a measurement result or an operation information and a unit for inputting an operation, an interface circuit 24 which controls transmission and reception of a signal to and from the ultrasonic probe 40, and a control substrate 30. In addition, an embedded battery (not shown) or the like is suitably provided.

A central processing unit (CPU) 31, an IC memory 32 in addition to various integrated circuits such as application specific integrated circuit (ASIC) or a field programmable gate array (FPGA), and a communication IC 33 which realizes data communication with an external device (ultrasonic probe 40 in this embodiment) through the interface circuit 24 are mounted on the control substrate 30. The control substrate 30 realizes various functions according to the embodiment such as ultrasonic measurement by executing control programs stored in the IC memory 32 such as the CPU 31.

That is, the ultrasonic measurement device 10 transmits and emits ultrasonic beams towards biological tissues from the ultrasonic probe 40 attached to the subject 2 and receives reflected waves, due to operation processes of the control substrate 30. It is possible to generate reflected wave data according to biological tissues of the subject 2 by amplifying and processing received signals of the reflected waves. The continuous measurement and the data storage of various biological information items are realized based on the reflected wave data items.

Figure 2:
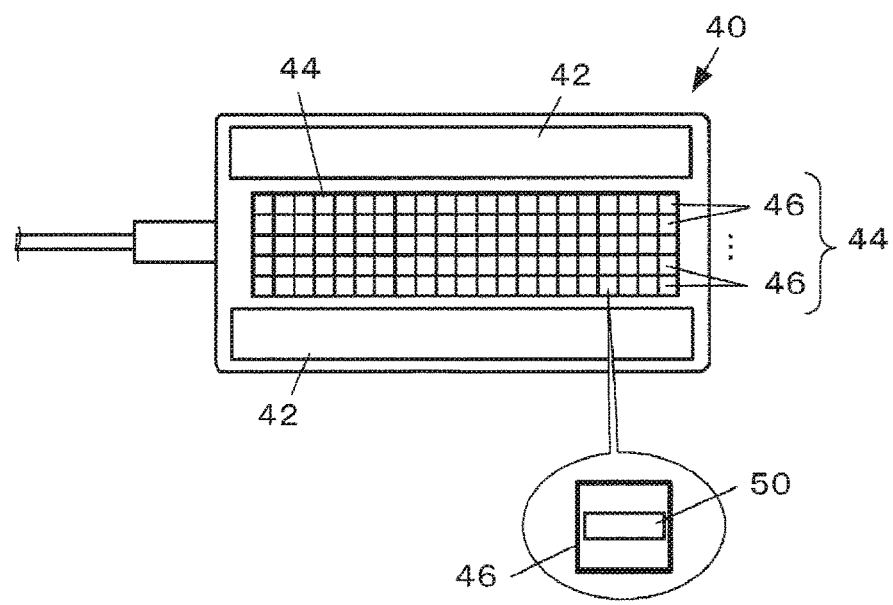
FIG. 2 is a view showing a configuration example of an ultrasonic probe of the first embodiment.

FIG. 2 is a view showing a configuration example of the ultrasonic probe 40 of the embodiment and is a view when seen from a side of the attached surface (ultrasonic transmission and reception surface) of the subject 2.

The ultrasonic probe 40 an bonding portion 42 which detachably bonds the ultrasonic probe 40 to skin of the subject 2, and an ultrasonic sensor 44 on the attached surface side.

The ultrasonic sensor 44 is an assembly a plurality of ultrasonic transducers 46 are two-dimensionally arranged in a long side direction and a short side direction of the ultrasonic transmission and reception surface. The ultrasonic probe 40 is attached to skin surface of the subject 2 in a relative position in which the long side of the ultrasonic sensor 44 crosses over the carotid 3 in a short axis direction.

One ultrasonic transducer 46 includes a piezoelectric element 50. The first piezoelectric element 50 is an element which physically (mechanically) moves, when a voltage is applied to a piezoelectric body, and an element which generates a voltage in accordance with an external force (ultrasonic waves in a case of this embodiment) received by a piezoelectric body. That is, in the embodiment, the piezoelectric element 50 performs both of transmission and reception of ultrasonic waves.

Figure 3:
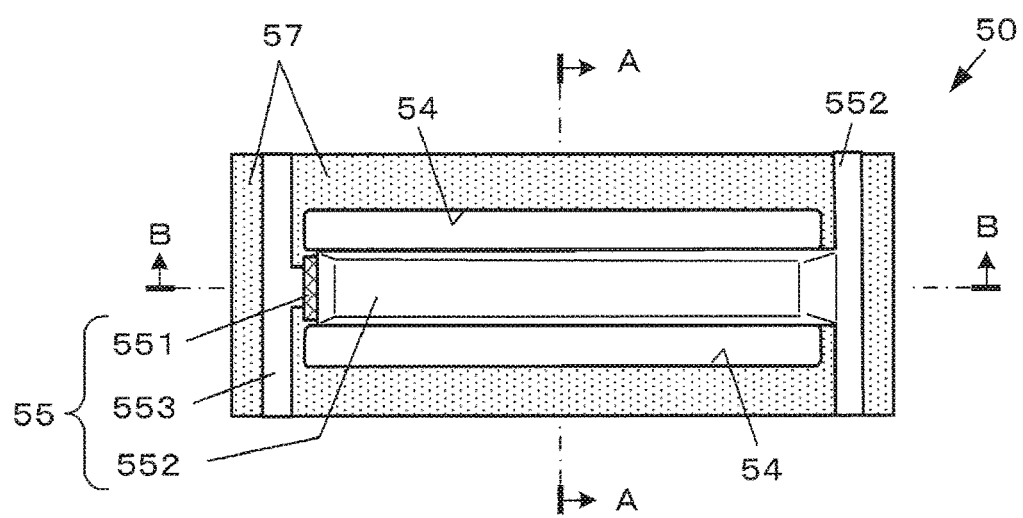
FIG. 3 is a top view showing a configuration example of a second piezoelectric element of the first embodiment.
Figure 4:
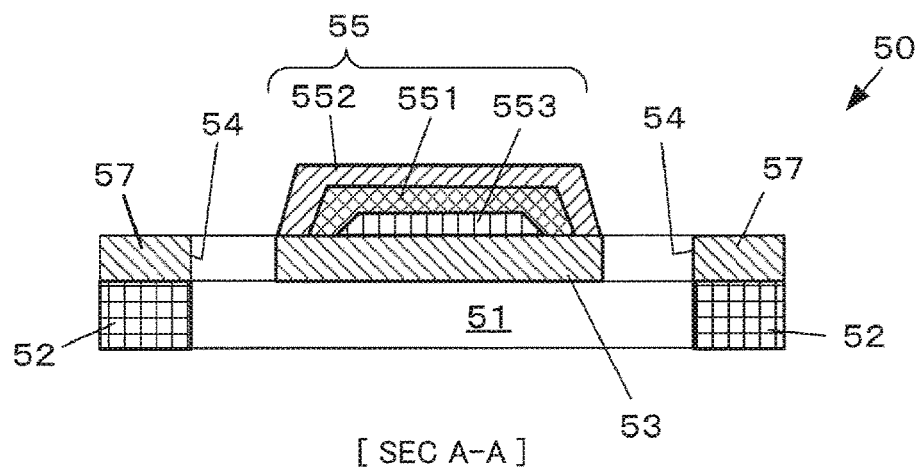
FIG. 4 is a sectional view taken along line A-A of FIG. 3.
Figure 5:
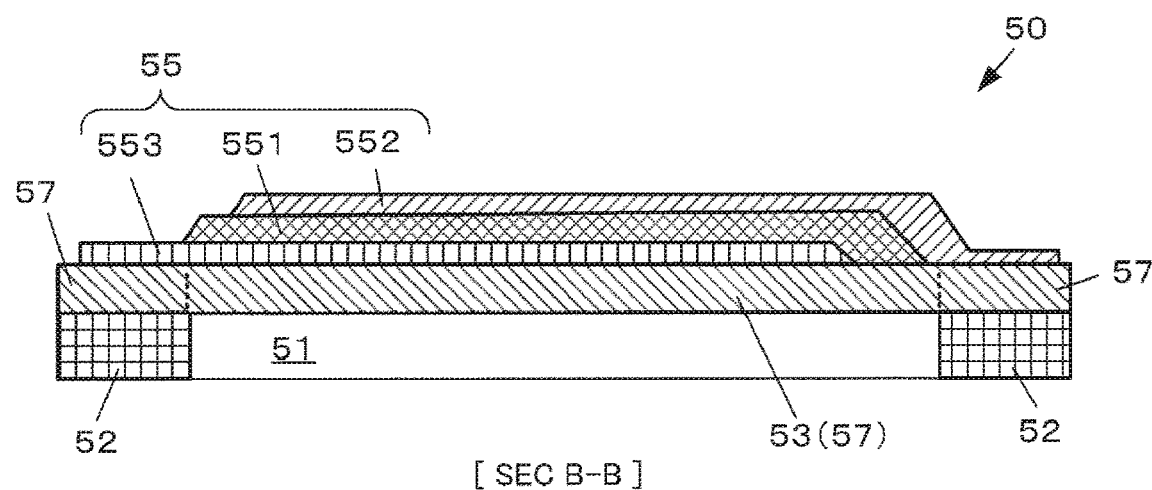
FIG. 5 is a sectional view taken along line B-B of FIG. 3.

FIG. 3 is a top view showing a configuration example of the piezoelectric element 50 of the embodiment. FIG. 4 is a sectional view taken along line A-A of FIG. 3. FIG. 5 is a sectional view taken along line B-B of FIG. 3.

The piezoelectric element 50 of the embodiment is an element which physically (mechanically) moves, when a voltage is applied to a piezoelectric body. More specifically, the piezoelectric element is an element which expands and contracts in accordance with a voltage. In the piezoelectric element 50 of the embodiment, a thin film-shaped silicon layer 57 is bonded to an upper surface of a support substrate 52 which has a rectangular shape in a top view and where a hollow portion 51 is provided (hollow portion 51 is opened). In addition, the hollow portion 51 may be formed after forming the silicon layer 57 on the upper surface of the support substrate 52.

The silicon layer 57 includes a vibrating plate 53 having a both-end supported beam structure (both-end fixed support structure) which crosses the hollow portion 51. That is, the silicon layer 57 is bonded so as to cover the hollow portion 51, and two slits 54 are provided along an edge portion of the hollow portion 51 having a rectangular shape in a top view in the longitudinal direction. These two slits 54 precisely realize a bridge structure of a thin plate, that is, both cantilever beams of a thin film which crosses the hollow portion 51 in the longitudinal direction.

A piezoelectric conversion unit 55 is laminated on the upper surface of the vibrating plate 53. The piezoelectric conversion unit 55 of the embodiment is configured by interposing a piezoelectric body 551 which performs energy conversion between electric energy and movement energy, between an upper electrode 552 and a lower electrode 553. In the embodiment, as the piezoelectric body 551, piezoelectric ceramic or lead zirconate titanate (PZT) is used, but other piezoelectric materials can be suitably selected.

When the AC voltage is applied between the upper electrode 552 and the lower electrode 553, the piezoelectric body 551 and the vibrating plate 53 periodically expand and contract in a high expansion and contraction direction (in the configuration of the embodiment, longitudinal direction of the vibrating plate 53). That is, the piezoelectric conversion unit 55 and the vibrating plate 53 are vibrated. Accordingly, the piezoelectric element 50 transmits ultrasonic waves to the upper side thereof (front side of FIG. 3 and upper side of FIG. 4 and FIG. 5) and the lower side thereof (rear surface side of FIG. 3 and lower side of FIG. 4 and FIG. 5).

The ultrasonic waves generated from the piezoelectric element 50 are reflected in the body of the subject 2 to become reflected waves and the piezoelectric element 50 receives the reflected waves from the upper or lower side thereof. When the reflected waves are received, the piezoelectric conversion unit 55 and the vibrating plate 53 integrally formed are warped, charges according to the warped amount are generated in the piezoelectric body 551, and a gap is generated between the upper electrode 552 and the lower electrode 553. The ultrasonic measurement device 10 calculates the biological information by performing the operation process of the voltage by the measurement control device 20.

The conversion efficiency of the piezoelectric element 50 when transmitting ultrasonic waves is dependent on elastic properties of the vibrating plate 53, in addition to the piezoelectric conversion unit 55. In the same manner, reception sensitivity when receiving ultrasonic waves is also dependent on elastic properties of the vibrating plate 53. In the related art, since the piezoelectric element used for transmitting and receiving ultrasonic waves is patterned and cut so as to cut a large number of piezoelectric elements as many as possible from a single crystal silicon wafer of plane orientation [001], a difference in elastic properties of a vibrating plate occurs depending on the patterning state, and a difference in elastic properties becomes a reason of a variation in properties of a piezoelectric element.

Figure 6:
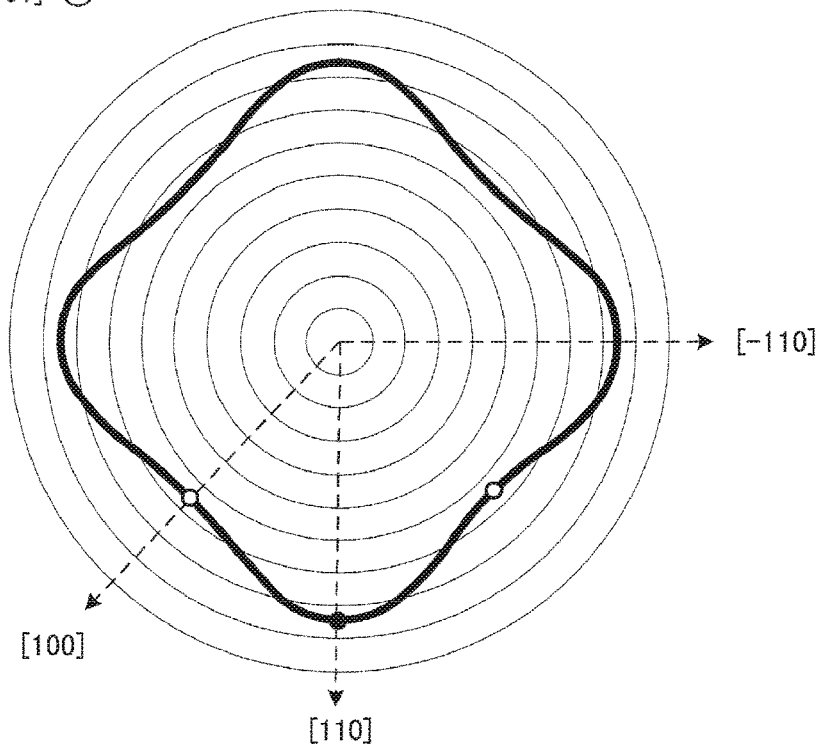
FIG. 6 is a graph showing an example of anisotropy of a Young's modulus of the [001] plane of single crystal silicon.

More specifically, FIG. 6 is a graph showing an example of anisotropy of a Young's modulus of the [001] plane of single crystal silicon. A front direction of FIG. 6 is shown as plane orientation [001] and a lower side of FIG. 6 is shown as plane orientation [110]. As shown in FIG. 6, the Young's modulus of the [001] plane of the single crystal silicon has anisotropy shown with a rhombic shape in which each center of four sides is slightly recessed to the inner side. Accordingly, when the plurality of piezoelectric elements 50 are horizontally and vertically arranged and patterned on the single crystal silicon wafer of plane orientation [001], the properties thereof changes and a variation therein occurs depending on orientation of a high expansion and contraction direction of the vibrating plate 53 (longitudinal direction of the vibrating plate 53, in the embodiment) of the piezoelectric element 50.

For example, a piezoelectric element in which a high expansion and contraction direction of the vibrating plate 53 (longitudinal direction of the vibrating plate 53, in the embodiment) is along low Young's modulus orientation [100] in which a Young's modulus is relatively low, includes the vibrating plate 53 which is easily warped, compared to that in a piezoelectric element in which the high expansion and contraction direction of the vibrating plate 53 is along high Young's modulus orientation [−110]. Accordingly, stronger ultrasonic waves are generated, even when the same voltage is applied to the piezoelectric element 50.

Figure 7:
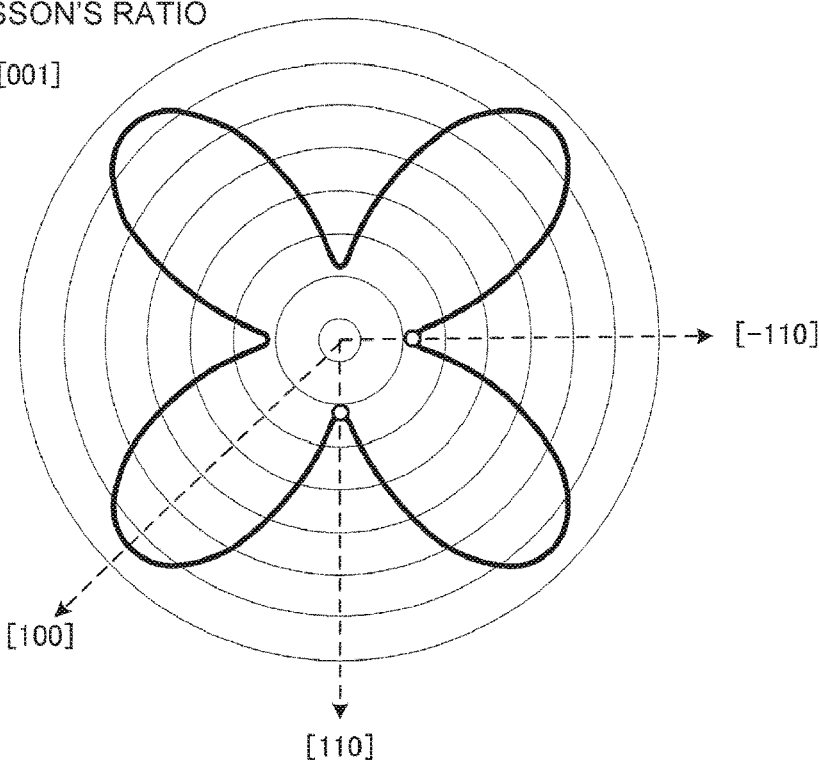
FIG. 7 is a graph showing an example of anisotropy of a Poisson's ratio of the [001] plane of single crystal silicon.

FIG. 7 is a graph showing an example of anisotropy of a Poisson's ratio of the [001] plane of single crystal silicon. A front direction of FIG. 7 is shown as plane orientation [001] and a lower side of FIG. 7 is shown as plane orientation [110]. As shown in FIG. 7, the Poisson's ratio of the [001] plane of the single crystal silicon has anisotropy shown with a four-leaf clover shape. Accordingly, when the plurality of piezoelectric elements 50 are horizontally and vertically arranged and patterned on the single crystal silicon wafer of plane orientation [001], the properties thereof changes and a variation therein occurs depending on orientation of a high expansion and contraction direction of the vibrating plate 53 of the piezoelectric element 50.

In a piezoelectric element in which the high expansion and contraction direction of the vibrating plate 53 is along low Poisson's ratio orientation [−110] in which a Poisson's ratio is relatively low, a so-called taut state is obtained and reception sensitivity when ultrasonic waves is received becomes high, compared to a piezoelectric element in which the high expansion and contraction direction of the vibrating plate 53 is along high Poisson's ratio orientation [100].

Therefore, in the embodiment, in order to prevent such a variation, the piezoelectric element 50 is prepared with a single crystal silicon wafer of plane orientation [111] having no anisotropy in a Young's modulus and a Poisson's ratio due to a deviation angle.

Figure 8:
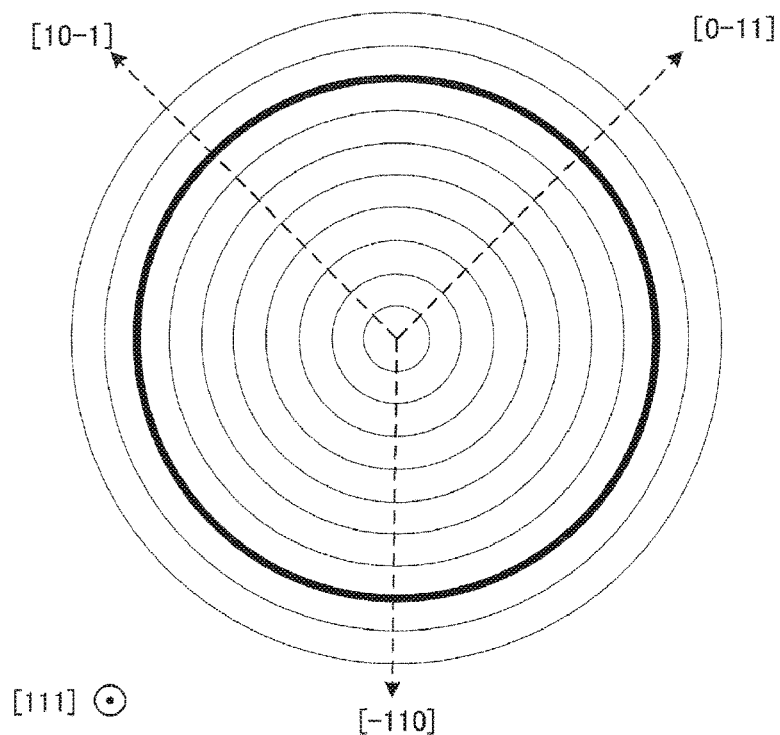
FIG. 8 is a graph showing an example of isotropy of a Young's modulus of the [111] plane of single crystal silicon.
Figure 9:
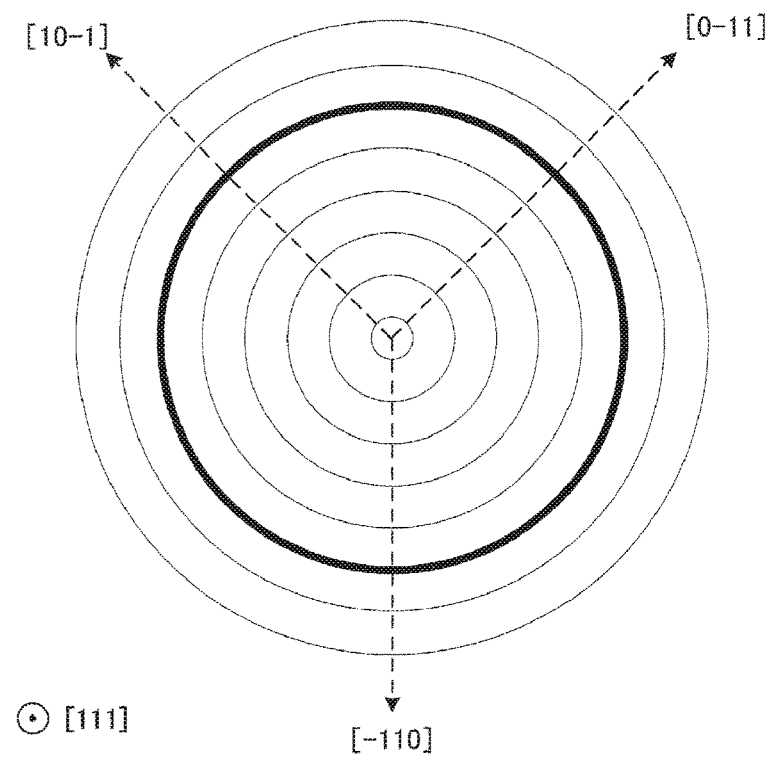
FIG. 9 is a graph showing an example of isotropy of a Poisson's ratio of the [111] plane of single crystal silicon.

FIG. 8 is a graph showing an example of isotropy of a Young's modulus of the [111] plane of single crystal silicon. A front direction of FIG. 8 is shown as plane orientation [111] and a lower side of FIG. 8 is shown as plane orientation [−110]. FIG. 9 is a graph showing an example of isotropy of a Poisson's ratio of the [111] plane of single crystal silicon. A front direction of FIG. 9 is shown as plane orientation [111] and a lower side of FIG. 9 is shown as plane orientation [−110].

As shown in FIG. 8 and FIG. 9, a single silicon wafer of the plane orientation [111] has no anisotropy in a Young's modulus and a Poisson's ratio due to a deviation angle. That is, even when the piezoelectric element 50 is patterned in any state, it is possible to prevent a variation in properties due to anisotropy of a silicon wafer.

Figure 10:
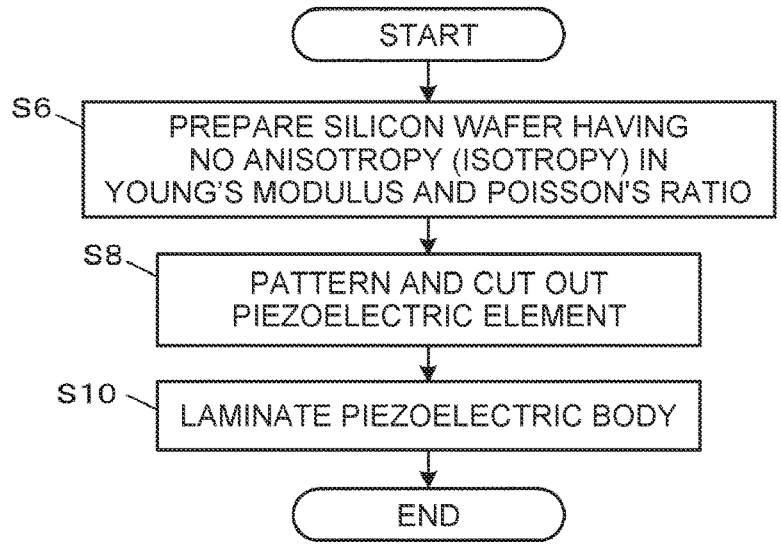
FIG. 10 is a flowchart for illustrating a manufacturing step of the piezoelectric element of the first embodiment.

FIG. 10 is a flowchart for illustrating a manufacturing step of the piezoelectric element 50 of the embodiment. First, in the manufacturing step of the piezoelectric element 50 of the embodiment, a silicon wafer 7 is prepared by slicing a single crystal silicon ingot in the [111] plane orientation having no anisotropy in a Young's modulus and a Poisson's ratio (that is, having isotropic elastic properties represented by a Young's modulus and a Poisson's ratio) (Step S6). The silicon wafer 7 is not only prepared by slicing the single crystal silicon ingot, but may be prepared by separately purchasing the silicon wafer 7 in the [111] plane orientation.

Next, the piezoelectric element 50 is patterned on the silicon wafer 7 and the silicon layer 57 of the piezoelectric element 50 including a material of the vibrating plate 53 is cut out (Step S8). Then, the piezoelectric element 50 is prepared by laminating the piezoelectric body 551 including the upper electrode 552 and the lower electrode 553, and the vibrating plate 53 (Step S10).

Figure 11:
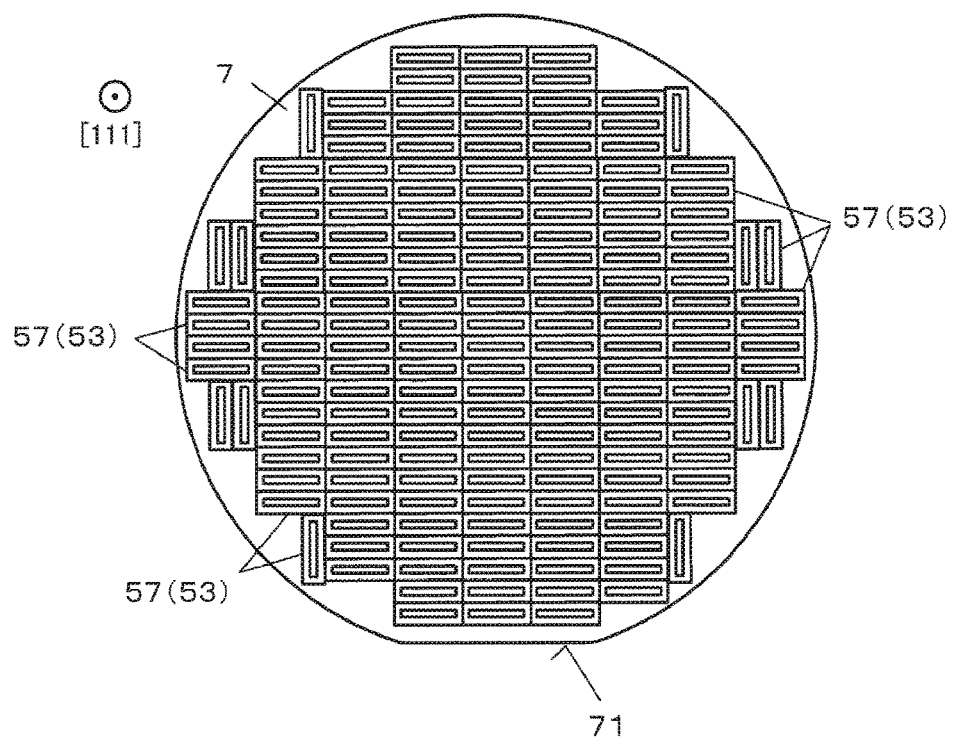
FIG. 11 is a perspective view for illustrating a positional relationship of patterning of a silicon layer and a vibrating plate of a piezoelectric element of a [111]-orientated silicon wafer.

FIG. 11 is a perspective view for illustrating a positional relationship of patterning of the piezoelectric element 50 of the silicon wafer 7 of [111] plane orientation of the embodiment, more specifically, patterning of the silicon layer 57 including the vibrating plate 53. An orientation flat 71 is formed on the edge portions corresponding to predetermined orientation in the [111]-oriented silicon wafer 7. Accordingly, the silicon layer 57 of each piezoelectric element 50 can be patterned by using the orientation flat 71 as a mark. However, since the [111]-oriented silicon wafer 7 has no anisotropy (that is, isotropy), a direction of patterning of each silicon layer 57 of the piezoelectric element 50 may be an arbitrary direction. It is possible to have equivalent elastic properties of the piezoelectric element 50, regardless of a cut-out state.

Hereinabove, according to the embodiment, it is possible to realize the piezoelectric element 50 in which variations in properties due to anisotropy of elastic properties of a silicon wafer is prevented, the ultrasonic probe 40 using the piezoelectric element, and the ultrasonic measurement device 10 using the piezoelectric element.

The laminated structure of the piezoelectric element 50 of the embodiment is used, but a configuration of further providing a thin film sheet layer on the upper surface side may be used.

Second Embodiment

Next, a second embodiment to which the invention is applied will be described.

This embodiment is basically realized in the same manner as in the first embodiment, but the structure of the piezoelectric element is different. Hereinafter, the differences from the first embodiment will be described and the same reference numerals are used for the same constituent elements and the description thereof will be omitted.

Figure 12:
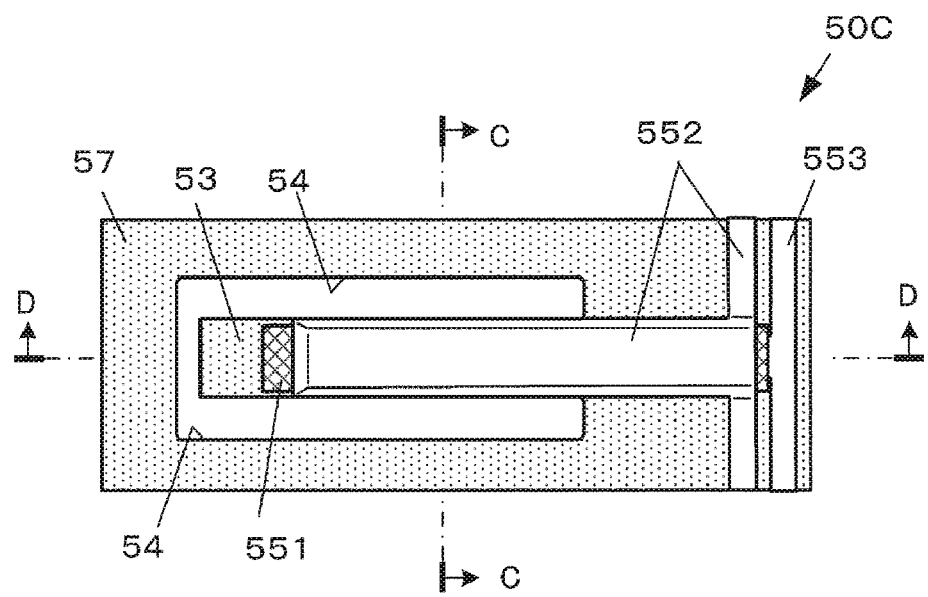
FIG. 12 is a top view showing a configuration example of a piezoelectric element of a second embodiment.
Figure 13:
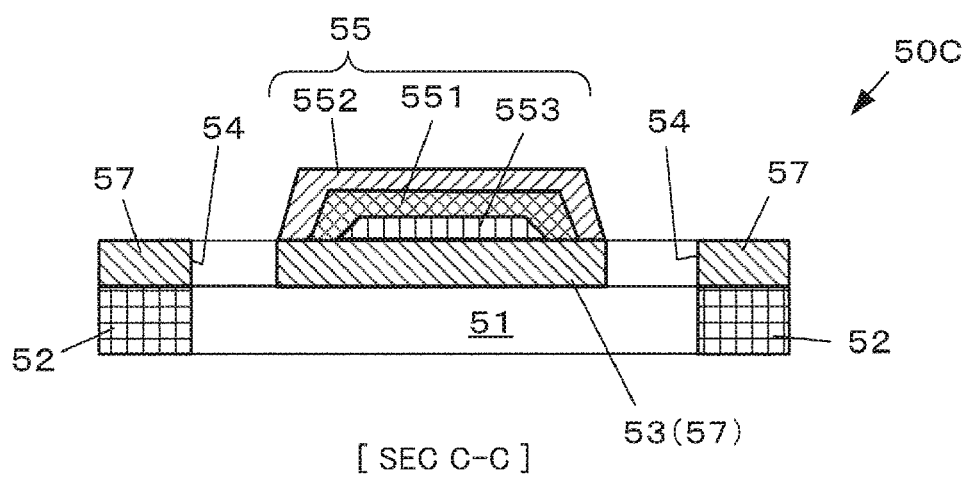
FIG. 13 is a sectional view taken along line C-C of FIG. 12.
Figure 14:
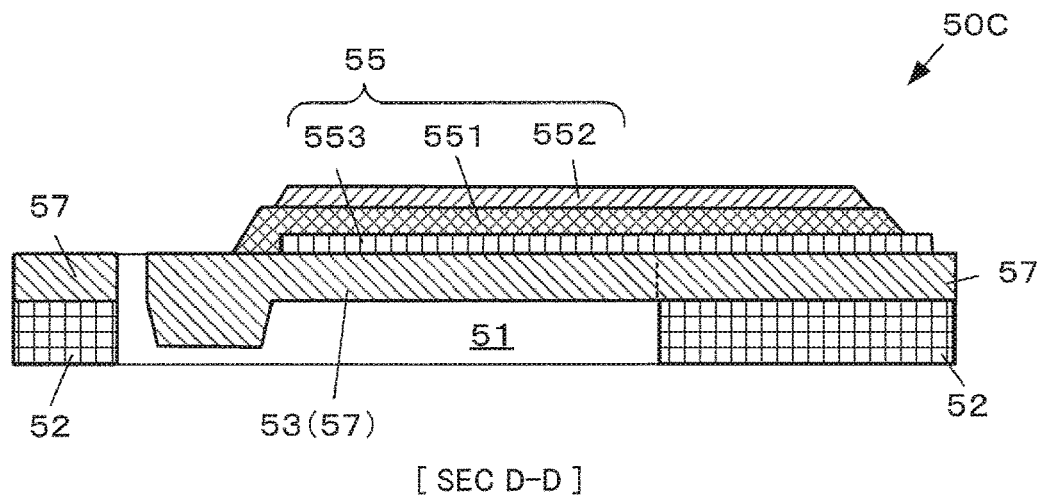
FIG. 14 is a sectional view taken along line D-D of FIG. 12.

FIG. 12 is a top view showing a configuration example of a piezoelectric element 50C of the embodiment. FIG. 13 is a sectional view taken along line C-C of FIG. 12. FIG. 14 is a sectional view taken along line D-D of FIG. 12. In the piezoelectric element 50C of the embodiment, a cantilever beam structure of a thin plate in which the vibrating plate 53 is extended to the hollow portion 51 is formed.

The patterning of the silicon wafer 7 of the silicon layer 57 including the vibrating plate 53 is performed in the same manner as in the first embodiment.

MODIFICATION EXAMPLES

Hereinabove, the embodiments to which the invention is applied have been described, but adding, omission, and modification of the constituent elements can be suitably performed.

First Example

Figure 15:
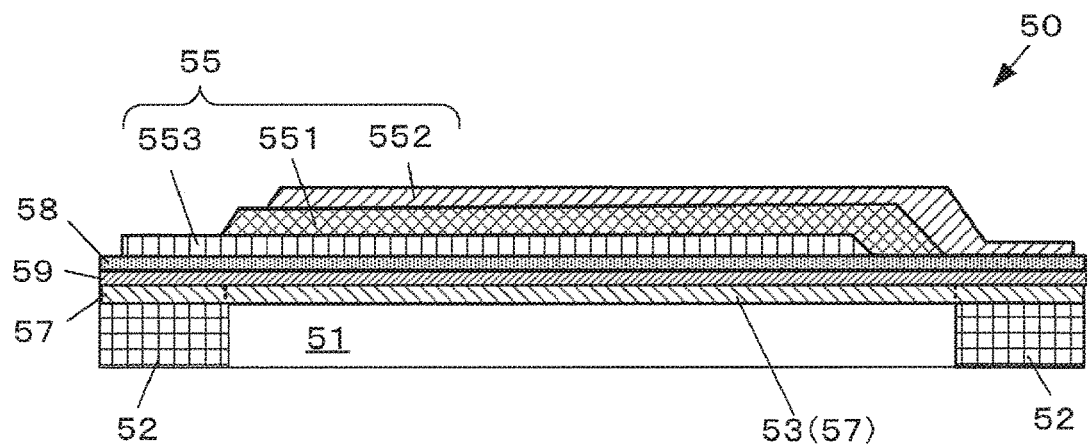
FIG. 15 is a sectional view showing a modification example of a configuration of the piezoelectric element (first example).

For example, in the embodiments described above, the vibrating plate 53 has a single-layer structure of silicon, but as shown in a vibrating plate longitudinal direction sectional view of FIG. 15 (corresponding to FIG. 5), a multi-layer structure including a zirconia oxide layer 58 or a silicon dioxide layer 59 between the vibrating plate and the piezoelectric conversion unit 55 may be used.

Second Example

Figure 16:
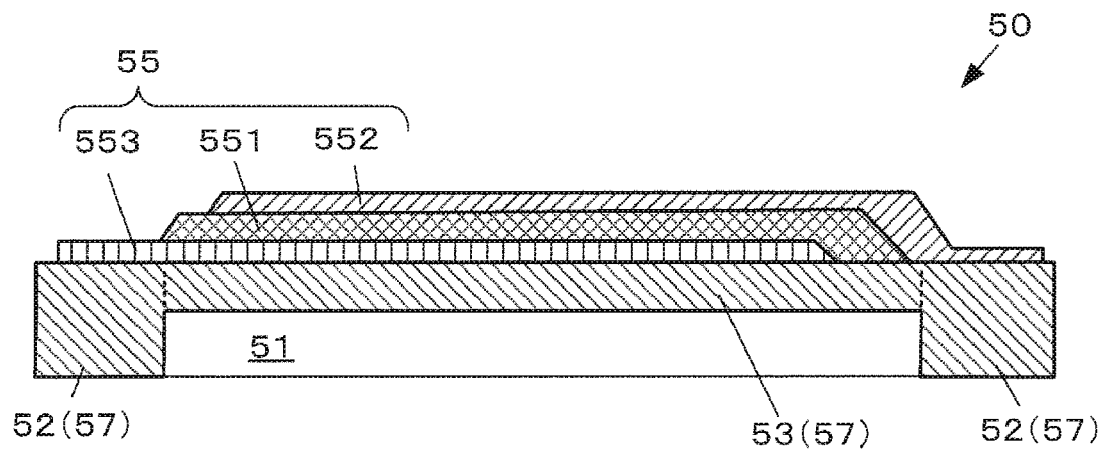
FIG. 16 is a sectional view showing a modification example of a configuration of the piezoelectric element (second example).

In the embodiments described above, the support substrate 52 and the silicon layer 57 are separate materials, but as shown in a vibrating plate longitudinal direction sectional view of FIG. 16, the same material is used for the support substrate 52 and the silicon layer 57, and the hollow portion 51 may be prepared by etching or the like.

Third Example

Figure 17:
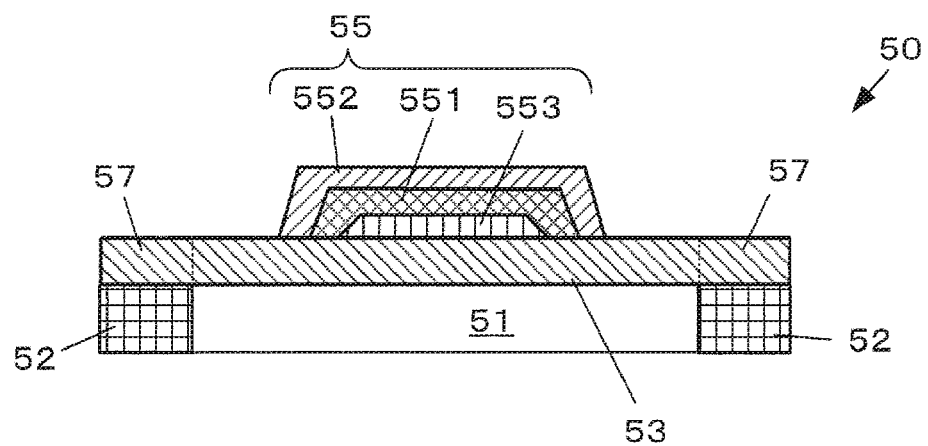
FIG. 17 is a sectional view showing a modification example of a configuration of the piezoelectric element (third example).

In the embodiments described above, the slits 54 are provided around the vibrating plate 53, but as shown in the sectional view of FIG. 17 (corresponding to FIG. 4), the slits 54 may be omitted. For example, when the vibrating plate 53 has a rectangular shape in a top view, a support structure in which the four sides are supported by the support substrate 52 can be used.

Fourth Example

Figure 18:
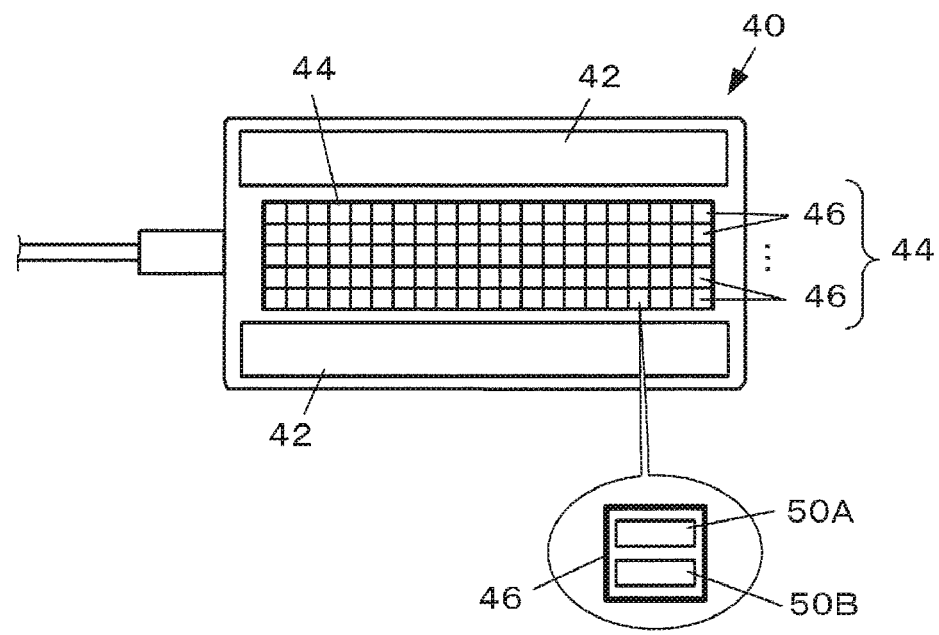
FIG. 18 is a view showing a modification example of a configuration of an ultrasonic probe.

In the embodiments described above, each piezoelectric element 50 has a configuration of performing transmission and reception of ultrasonic waves, but for example, as shown in FIG. 18, a first piezoelectric element 50A for transmitting ultrasonic waves and a second piezoelectric element 50B for receiving ultrasonic waves can be separately provided in one ultrasonic transducer 46. In this case, it is possible to use the piezoelectric element 50 according to any one or both of the embodiments.

Fifth Example

In the embodiment described above, single crystal silicon is used as the material of the vibrating plate 53, but other materials may be used as long as they are materials capable of preparing a thin plate in the crystal orientation plane having isotropy of and a Young's modulus and a Poisson's ratio in a deviation angle direction. For example, a material such as other elements belong to carbon family (elements of Group 14) can be used in the same manner as silicon such as gallium arsenide.

Sixth Example

Figure 19:
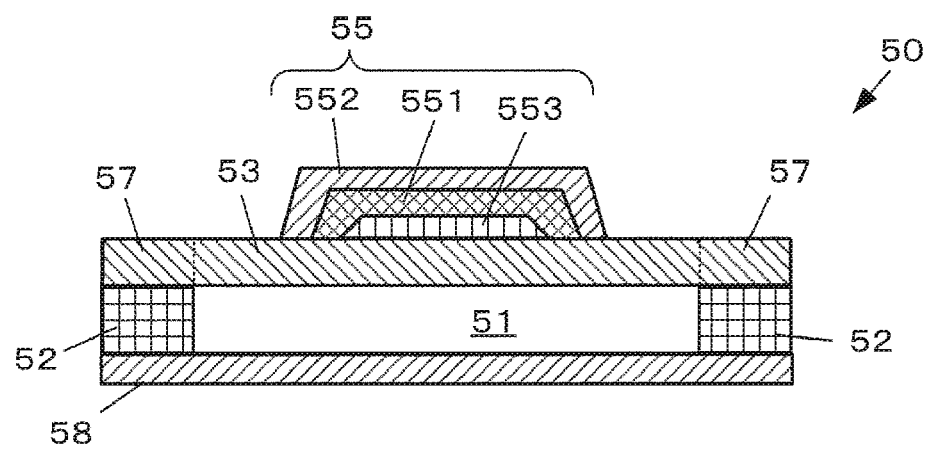
FIG. 19 is a sectional view showing a modification example of a configuration of the piezoelectric element (fourth example).

In the embodiments described above, the lower surface side of the hollow portion 51 is opened, but as shown in FIG. 19, the hollow portion 51 may be provided as an enclosed region by suitably providing a backing plate 58.

Figure 20:
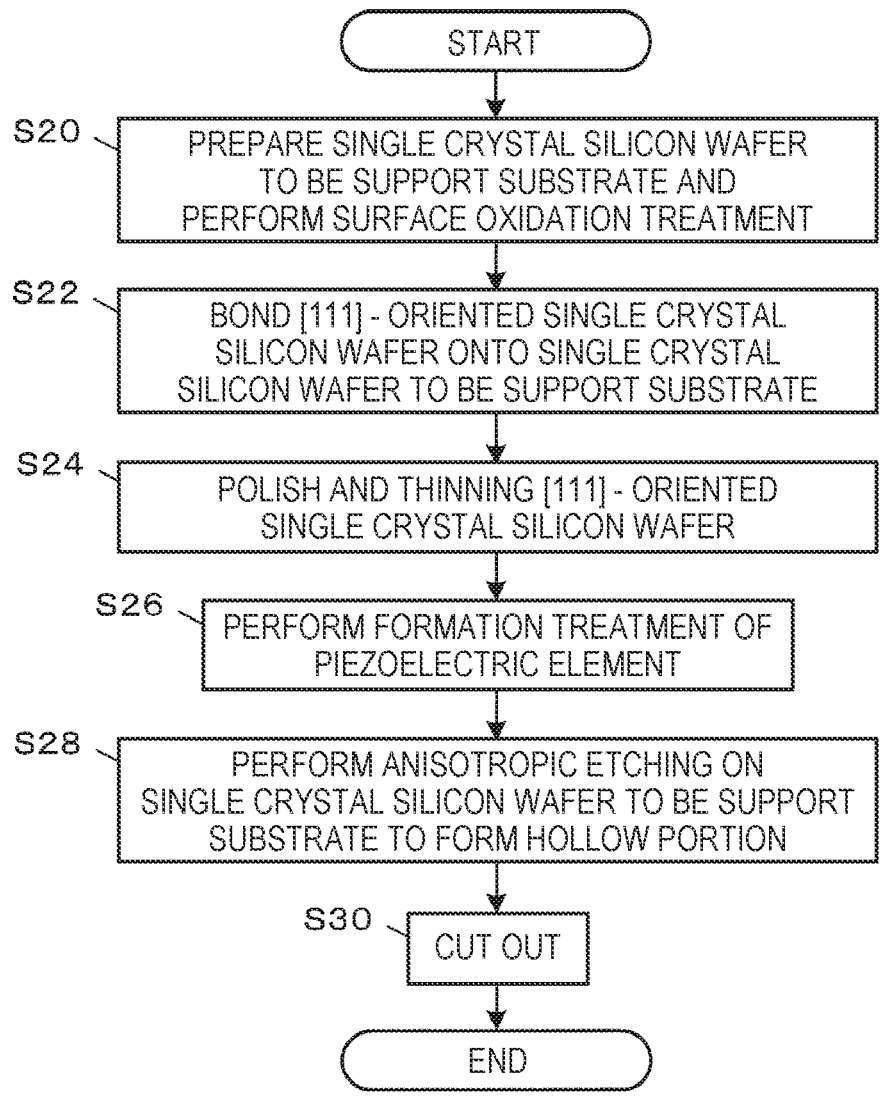
FIG. 20 is a flowchart for illustrating a manufacturing step of a piezoelectric element in a case of using anisotropic etching.

In a case of preparing the silicon layer 57 by using the [111]-oriented single crystal silicon and preparing the support substrate 52 by using another oriented single crystal silicon, it is possible to realize the piezoelectric element 50 having the configuration described above by a silicon on insulator (SOI) process using anisotropy etching shown in FIG. 20.

Specifically, the single crystal silicon wafer (for example, [110]-oriented single crystal silicon wafer) to be the support substrate 52 is prepared and surface oxidation treatment is performed (Step S20).

Next, the [111]-oriented single crystal silicon wafer having no anisotropy in a Young's modulus and a Poisson's ratio is prepared and bonded to the upper surface side of the single crystal silicon wafer to be the support substrate 52 which is previously prepared (Step S22), and the [111]-oriented single crystal silicon wafer is polished and thinned to prepare the silicon layer 57 (Step S24).

Next, the piezoelectric element 55 is prepared on the [111]-oriented single crystal silicon wafer (Step S26) and the single crystal silicon wafer to be the support substrate 52 is subjected to anisotropy etching (for example, so-called KOH etching using potassium hydroxide) to form the hollow portion 51 (Step S28). After performing formation treatment of a backing plate 58 (Step S28), the cut-out is performed (Step S30).

When Step S28 is omitted, it is also possible to suitably apply the manufacturing processes in the preparation of the piezoelectric element having other configurations described in this specification.

The entire disclosure of Japanese Patent Application No. 2015-229831 filed on Nov. 25, 2015 is expressly incorporated by reference herein.

What is claimed is:
1. A piezoelectric element comprising:
   a piezoelectric body;
   a vibrating plate having [111]-oriented single crystal silicon as a vibrating material laminated on the piezoelectric body; and a support substrate bonded to the vibrating plate,
wherein the support substrate includes a hollow portion at a position overlapped with the piezoelectric body in a plan view in a thickness direction of the support substrate, and
wherein the vibrating plate has a two-end fixed supported beam structure forming a bridge and has two openings formed along an edge of the hollow portion.

2. The piezoelectric element according to claim 1, wherein a zirconia oxide layer and a silicon oxide layer are provided between the piezoelectric body and the vibrating plate.

3. An ultrasonic probe comprising:
the piezoelectric element according to claim 1 for transmitting ultrasonic waves.

4. An ultrasonic probe comprising:
the piezoelectric element according to claim 1 for receiving ultrasonic waves.

5. An ultrasonic probe comprising:
the piezoelectric element according to claim 1 for transmitting and receiving ultrasonic waves.

6. An ultrasonic measurement device comprising:
the ultrasonic probe according to claim 3.

7. A manufacturing method of a piezoelectric element comprising:
cutting out a vibrating material to be used in a vibrating plate from a oriented single crystal silicon wafer;
laminating the vibrating plate on a piezoelectric body;
bonding a support substrate to the vibrating plate,
wherein the support substrate includes a hollow portion at a position overlapped with the piezoelectric body in a plan view in a thickness direction of the support substrate, and
wherein the vibrating plate has a two-end fixed supported beam structure forming a bridge and has two openings formed along an edge of the hollow portion.

* * * * *